United States Patent [19]
Haneda et al.

[11] Patent Number: 4,783,557
[45] Date of Patent: Nov. 8, 1988

[54] PROCESSES FOR PREPARING HYDROXYNAPHTHALENES

[75] Inventors: Yutaka Haneda, Osaka; Sadao Yoshimoto; Hisaya Miki; Masaaki Yasuda; Shintarou Araki, all of Yamaguchi; Masatoshi Nitabaru, Hiroshima, all of Japan

[73] Assignee: Mitsui Petrochemical Industries, Ltd., Tokyo, Japan

[21] Appl. No.: 94,883

[22] Filed: Sep. 10, 1987

[30] Foreign Application Priority Data

Sep. 12, 1986 [JP] Japan .................. 61-215160
Apr. 2, 1987 [JP] Japan .................. 62-79734
Jun. 12, 1987 [JP] Japan .................. 62-146445

[51] Int. Cl.$^4$ .......................... C07C 37/08
[52] U.S. Cl. ........................ 568/741; 568/735
[58] Field of Search ............ 568/741, 735, 572, 573, 568/574, 575

[56] References Cited

U.S. PATENT DOCUMENTS

| | | | |
|---|---|---|---|
| 2,749,368 | 6/1956 | Fortuin et al. | 568/575 |
| 2,751,418 | 6/1956 | Enos | 568/575 |
| 2,771,491 | 11/1956 | Conner Jr. | 568/741 |
| 2,776,322 | 1/1957 | Webster et al. | 568/741 |
| 2,985,687 | 5/1961 | Thelin et al. | 568/741 |
| 4,463,198 | 7/1984 | Nowak et al. | 568/741 |
| 4,503,262 | 3/1985 | Gupton et al. | 568/575 |

FOREIGN PATENT DOCUMENTS 2517591 10/1975 Fed. Rep. of Germany ...... 568/741

Primary Examiner—Werren B. Lone
Attorney, Agent, or Firm—Wenderoth, Lind & Ponack

[57] ABSTRACT

Disclosed in accordance with the present invention are processes for the preparation of hydroperoxides and/or carbinols by liquid phase oxidation of secondary alkyl-substituted naphthalenes with molecular oxygen, wherein the oxidation reaction is carried out by dissolving in the reaction mixture containing the secondary alkyl-substituted naphthalenes at least 0.5 ppm in terms of metal, based on the starting secondary alkyl-substituted naphthalenes, of at least one compound of metal selected from the group consisting of palladium and gold, said metal compound being soluble in the reaction mixture of the secondary alkyl-substituted naphthalenes. When compared with the prior art processes using catalysts of non-homogeneous system, therefore, not only the amount of catalyst used can be minimized but also the rate of oxidation can be enhanced, and hence there can be obtained in a short period of time hydroperoxides and/or carbinols in high yields which are the oxidation products in accordance with the present invention.

According to the present invention, the desired hydroperoxide can be obtained in high yields as well as in high purity from the hydroperoxides and/or carbinols obtained in the manner as mentioned above.

5 Claims, No Drawings

PROCESSES FOR PREPARING HYDROXYNAPHTHALENES

FIELD OF THE INVENTION

This invention relates to processes for preparing hydroxynaphthalene and more particularly to processes for preparing hydroxynaphthalene by oxidizing secondary alkyl-substituted naphthalenes with molecular oxygen in the presence of catalysts to form hydroperoxides and/or carbinols of naphthalenes, from which the hydroxynaphthalene is then prepared.

BACKGROUND OF THE INVENTION

Dihydroxynaphthalene may be prepared by oxidizing secondary alkyl-substituted naphthalenes, for example, diisopropylnaphthalene, to diisopropylnaphthalene dihydroperoxide (hereinafter sometimes called DHP for short) which is then subjected to acid decomposition with acid catalysts. Furthermore, diisopropylnaphthalene dicarbinol formed at the time of oxidation of diisopropylnaphthalene may be oxidized with hydrogen peroxide to DHP. This dihydroxynaphthalene is an industrially useful starting material for preparing various products, for example, synthetic resins, synthetic fibers, medicines, agricultural chemicals, dyes, etc.

U.S. Pat. No. 4,503,262 discloses to the effect that in a process for preparing DHP by oxidation of solutions of diisopropylnaphthalene in organic solvents with molecular oxygen in the presence of heavy metal catalysts, for example, cobalt salts of organic acids, the reaction rate, the yield and purity of the desired dihydroperoxide may be improved by using as the above-mentioned organic solvents, particularly aliphatic hydrocarbon solvents of 5-14 carbon atoms, for example, n-heptane. In the process as disclosed, however, the alleged improvement in the reaction rate or yield is not always to be satisfactory.

Furthermore, U.S. Pat. No. 2,751,418 discloses a process for preparing hydroperoxide by oxidation of secondary alkyl-substituted aromatic hydrocarbons with molecular oxygen in the presence of heavy metal catalysts such as palladium, platinum, osmium, iridium, ruthenium, rhodium, etc. In the process disclosed in said patent, however, the catalysts used are of so-called nonhomogeneous system, that is, they are those which have carried nobel metals on solid carriers, for example, alumina etc., or solid catalyst with a large catalyst surface area such as colloidal palladium, and these catalysts are dispersed in reaction solution. This patent fails to teach concretely in examples thereof the oxidation of secondary alkyl-substituted naphthalenes, though the patent discloses examples showing oxidation of alkylbenzene such as p-thymene, sec-butylbenzene, etc. In the oxidation reaction shown in the examples of this patent, such weak base as sodium hydrogene carbonate or sodium carbonate is used as the base, and accordingly said oxidation reaction is carried out only in the reaction solution of a low pH range.

British Patent No. 714,545 discloses to the effect that in the preparation of hydroperoxide by oxidation of secondary alkyl-substituted aromatic hydrocarbons with molecular oxygen, the oxidation ratio is improved when the oxidation reaction is carried out by using a reactor, the inner surface of which has been coated with copper, silver or gold, or stirring blades covered on the surface thereof with said metal. This patent, however, only discloses examples thereof wherein alkylbenzene such as cumene, diisopropylbenzene, etc. is oxidized with a reactor covered on the inner surface thereof with copper, and the effect as alleged to be obtainable thereby is found to be still insufficient.

British Patent No. 760,367 discloses a process for obtaining hydroperoxide by oxidation of cumene in the presence of copper formate or silver acetate, but the effect of the process is still insufficient.

In practicing the oxidation of secondary alkyl-substituted naphthalenes, the present inventors investigated the processes as disclosed in the above-mentioned patents and have ascertained that the oxidation reaction of the secondary alkyl-substituted naphthalenes cannot be carried out at a satisfactory rate even when any of the disclosed processes is employed therefor.

Further, it has been found that it was difficult to obtain hydroxynaphthalene in high purity as well as in high yields by subjecting a reaction mixture obtained by liquid phase oxidation of secondary alkyl-substituted naphthalenes with molecular oxygen to acid decomposition. Accordingly, it is of extremely high commercial value if hydroxynaphthalene can be obtained in high purity and in high yields from the above-mentioned oxidation reaction mixture.

Still further, Japanese Patent Laid-Open-to-Public Publication No. 282333/1986 discloses a process for preparing 2,6-dihydroxynaphthalene by one-state oxidation and acid decomposition of 2,6-diisopropylnaphthalene dicarbinol with hydrogen peroxide in acetonitrile or dioxane in the presence of inorganic acids. In this process, however, the starting substance to be subjected to the reaction is dicarbinol in its purified form free from impurities.

OBJECT OF THE INVENTION

The present invention is to solve such problems associated with the prior art as mentioned above. In the oxidation of secondary alkyl-substituted naphthalenes with molecular oxygen to form hydroperoxides and/or carbinols, from which the desired hydroxynaphthalene is prepared, an object of the present invention is to provide a process for obtaining the desired hydroperoxides and/or carbinols in high yields as well as in high selectivity, which involves the oxidation reaction that is made faster in oxidation rate as compared with the prior art processes and that is complete in a short period of time by carrying out said oxidation reaction in the presence of specific catalysts selected.

A further object of the present invention is to provide a process for obtaining hydroxynaphthalene in high purity as well as in high yields from an oxidation reaction mixture containing hydroperoxides and/or carbinols obtained by oxidation of secondary alkyl-substituted naphthalene in the manner mentioned above.

SUMMARY OF THE INVENTION

The process for preparing hydroxynaphthalene of the present invention by liquid oxidation of secondary alkyl-substituted naphthalenes with molecular oxygen to form hydroperoxides and/or carbinols from which the desired hydroxynaphthalene is prepared, is characterized in that the oxidation reaction is carried out by dissolving in the reaction mixture of the secondary alkyl-substituted naphthalenes a metal compound which is soluble in said reaction mixture in an amount in terms of metal of at least 0.5 ppm based on the weight of the starting secondary alkyl-substituted naphthalenes.

Further, the process for preparing hydroxynaphthalene of the present invention is characterized in that the desired hydroxynaphthalene is obtained by decomposing the oxidation reaction mixture containing hydroperoxides and/or carbinols obtained by oxidation of secondary alkyl-substituted naphthalenes in the manner mentioned above with (c) an acid in the presence of at least one solvent selected from (a) nitriles, nitro compounds, phenols and halogenated hydrocarbons, and of (b) hydrogen peroxide.

Still further, the process for preparing hydroxynaphthalene of the present invention is characterized in that the oxidation reaction mixture containing hydroperoxides and/or carbinols obtained by oxidation of the secondary alkyl-substituted naphthalenes is decomposed with (c) an acid in the presence of at least one solvent selected from (a) nitriles, nitro compounds, phenols and halogenated hydrocarbons, and of (b) hydrogen peroxide to form hydroxynaphthalene, the acid decomposition reaction mixture containing the formed hydroxynaphthalene is reacted with an acyloxylating agent to form acyloxynaphthalene, and then the thus formed acyloxynaphthalene is hydrolyzed in a solvent containing water in the presence of an acid catalyst to form hydroxynaphthalene.

DETAILED DESCRIPTION OF THE INVENTION

The process for preparing hydroxynaphthalene of the present invention is illustrated below in detail.

In accordance with the present invention, hydroperoxides and/or carbinols are prepared by liquid phase oxidation of secondary alkyl-substituted naphthalenes with molecular oxygen. Exemplified as the secondary alkyl-substituted naphthalenes used in the above case are concretely, $\beta$-isopropylnaphthalene, $\beta$-sec-butylnaphthalene, 2,6-diisopropylnaphthalene, 2,7-diisopropylnaphthalene, 2,4-diisopropylnaphthalene, 2,6-di(sec-butyl)naphthalene, 1,7-di(sec-butyl)naphthalene, etc. Of these naphthalenes, preferred are isopropylnaphthalene and diisopropylnaphthalene, particularly 2,6-diisopropylnaphthalene.

In practicing the oxidation reaction in accordance with the present invention, the presence of a base is not always necessary, but usually the oxidation is preferably carried out in the presence of the base. Preferably usable as the bases in that case are alkali metal compounds. Such alkali metal compounds concretely include sodium hydroxide, potassium hydroxide, sodium carbonate, potassium carbonate, etc., which are conventionally known as the bases for use in the reactions of the kind. The alkali metal compounds are usually used in the form of aqueous solution thereof.

Concentrations of these alkali metal compounds in their aqueous solutions are preferably less than 20% by weight. Usually, the amount of an aqueous base solution used in the reaction mixture is preferably 5-80%, particularly 20-70% by weight of the reaction mixture. When the amount of the aqueous base solution is less than 5% by weight of the reaction mixture, the state of dispersion of oily unreacted secondary alkyl-substituted naphthalenes and oxidation products thereof relative to the reaction liquid consisting of the aqueous base solution becomes unfavorable, whereby the emulsified state of the reaction system becomes insufficient to exert an adverse effects on the oxidation reaction. On the other hand, the use of the aqueous base solution in an amount exceeding 80% by weight is not preferable as the emulsified state of the reaction system becomes poor. In the oxidation reaction, a pH of the aqueous base solution is usually maintained at least 7, preferably at least 12.

The starting secondary alkyl-substituted naphthalenes and the oxidation product thereof, and the aqueous base solution can be sufficiently emulsified usually by mechanical stirring, but, if necessary, they may be stirred together in the presence of conventionally known emulsifiers.

As the above-mentioned bases, there may also be used such alkaline earth metal hydroxides as calcium hydroxide, magnesium hydroxide. strontium hydroxide, etc. Particularly preferred is calcium hydroxide. These alkaline earth metal oxides may be used either singly or in combination with the above-mentioned alkali metal compounds.

In practicing the oxidation of secondary alkyl-substituted naphthalenes in accordance with the present invention, among the compounds as catalysts of at least one metal selected from the ground consisting of palladium and gold, used are the metal compounds which are soluble in the reaction mixture containing the starting secondary alkyl-substituted naphthalenes. Of such soluble metal compounds. palladium compounds which may be exemplified in concrete are inorganic palladium compounds such as palladium chloride, palladium sulfate, palladium nitrate, etc., or organic palladium compounds such as palladium acetylacetonate, palladium oxalate, palladium acetate, etc. Of these palladium compounds, preferrred is palladium chloride. As the gold compounds, there may be exemplified in concrete sodium chloraurate, aurous cyanide, gold chloride, potassium tetrachloraurate, sodium tetrachloraurate, potassium tetrahydroxoaurate, etc. Of these gold compounds, preferred is sodium chloraurate.

In the present invention, the oxidation reaction is carried out by dissolving in the reaction mixture containing the starting secondary alkyl-substituted naphthalenes the metal compound which is soluble in said reaction mixture in an amount in terms of metal of at least 0.5 ppm based on the weight of the starting secondary alkyl-substituted naphthalenes. The oxidation reaction in accordance with the present invention is illustrated below in detail.

In the present specification, by reaction mixture of secondary alkyl-substituted naphthalenes is meant a mixed solution containing a base, hydroperoxides and carbinols resulting from the oxidation of the secondary alkyl-substituted naphthalenes, and unreacted naphthalenes, that is, the mixed solution present in the reaction system during the time from the initiation of the oxidation reaction after charging the materials necessary for carrying out the reaction into a reactor up to the completion of the reaction. Accordingly, when no insolubles are present in the reaction mixture, the total volume of said reaction mixture corresponds to the reaction mixture solution in accordance with the present invention. Such reaction mixture solution as referred to above is illustrated below in more detail. When an aqueous solution of the above-mentioned alkali metal compound is used as the base, the reaction mixture solution forms an oil-water mixture consisting of two liquid phases, an oily phase and aqueous phase. In the present invention, the above-mentioned metal compound as the catalyst is used by dissolving it in the reaction mixture in an amount in terms of metal of at least 0.5 ppm based on the starting secondary alkyl-substituted naphthalenes. In that case, the metal compound may be dissolved in either the oily phase or the aqueous phase. For instance, the metal compound as the catalyst may be dissolved in only the oily phase or in the aqueous phase, or may be dissolved in both phases. In short, the oxidation reaction is carried out in such a manner that the metal compound as the catalyst is dissolved in either one of the oily and aqueous phase or both so that the total amount of the dissolved metal compound becomes at least 0.5 ppm in terms of metal based on the starting secondary alkyl-substituted naphthalenes.

In the present invention, the above-mentioned alkaline earth metal hydroxide as the base may be used in its powder form without using water. In this case, the above-mentioned reaction mixture solution forms only an oily phase, and the reaction can be carried out by dissolving in the oily phase the metal compound as the catalyst, for example, organic palladium compound such as palladium acetyl acetonate or the like.

In the present invention, the metal compound as the catalyst is used by dissolving it in the aforesaid reaction mixture solution in an amount of at least 0.5 ppm in terms of metal based on the starting secondary alkyl-substituted naphthalenes. In this respect, a further explanation is offered hereinafter. Where the oxidation reaction is carried out batchwise, the reaction is effected by dissolving the metal compound in the reaction mixture solution, when a reactor is charged with said reaction mixture solution, in an amount of at least 0.5 ppm in terms of metal based on the starting secondary alkyl-substituted naphthalenes. When the oxidation reaction is carried out continuously, the reaction is effected in such a manner that the amount of the metal compound becomes at least 0.5 ppm in terms of metal based on the total amount of unreacted secondary alkyl-substituted naphthalene to be recycled to the reaction zone and a fresh secondary alkyl-substituted naphthalene to be replenished.

In the present invention, the following procedure is preferably employed as the method of dissolving the metal compound in the aforesaid reaction mixture solution in an amount of at least 5 ppm in terms of metal based on the starting secondary alkyl-substituted naphthalenes. That is, the metal compound is first dissolved in a soluble solvent to prepare a catalyst solution having a suitable concentration, this solution is charged together with the base and secondary alkyl-substituted naphthalenes into an oxidation reactor, followed by mixing. According to this procedure, the oxidation reaction can be carried out satisfactorily by dissolving the predetermined amount of the metal compound assuredly in the reaction mixture solution from the point of initiation of the reaction. Such catalyst solution may be charged totally, prior to the initiation of the reaction, into the reactor to effect the reaction, or if necessary, a suitable amount of the catalyst solution is fed, after initiation of the reaction, into the reactor either continuously or intermittently to effect the reaction. In that case, it is preferable to use as the catalyst the metal compound which has been dissolved in a basic aqueous solution.

As soluble solvents for dissolving the metal compound, there may be used, in concrete, water, basic aqueous solutions, acid aqueous solutions or hydrocarbon solvents. Of these solvents, basic aqueous solutions are preferred for the reason mentioned above. Selection of preferred soluble solvents depends on the selection of the metal compound to be used. For instance, when palladium chloride is used as the catalyst, it is preferable to use water adjusted in pH to acidic or alkaline side by the addition of acid or base such as hydrochloric acid or sodium hydroxide, that is, acid aqueous solution or base aqueous solution, because palladium chloride is difficultly soluble in neutral water. When palladium sulfate is used as the catalyst, there may be used water around neutrality, acid aqueous solutions, and basic aqueous solution in which palladium sulfate can be dissolved. When such organic palladium compound as palladium acetyl acetonate is used as the catalyst, there may be used hydrocarbon solvents because organic palladium usually dissolves in alkylbenzenes or hydrocarbon solvents such as secondary alkyl-substituted naphthalenes which are used as starting materials in oxidation.

In the catalyst solutions obtained as above, the concentration of the dissolved metal compound is not particularly limited. That is, the concentration of the metal compound in the catalyst solution is not critical so long as the amount of the metal compound dissolved in the reaction mixture solution in the oxidation reaction which is carried out by charging the catalyst solution together with the base and the starting secondary alkyl-substituted naphthalenes into a reactor can be adjusted to at least 0.5 ppm in terms of metal based on the weight of the starting secondary alkyl-substituted naphthalenes. Usually, the catalyst solution is prepared by dissolving the metal compound in the aforesaid solvent so as to have a concentration of said metal compound of 10–1000 ppm in terms of metal, and when this catalyst solution is used. it is easy to adjust the amount of the metal compound dissolved in the reaction mixture solution to the amount of at least 0.5 ppm as aforesaid.

In the present invention, the oxidation of the secondary alkyl-substituted naphthalenes is carried out in the manner as mentioned above by dissolving the aforesaid metal compound in ihe reaction mixture solution so that the amount of the dissolved metal compound becomes at least 0.5 ppm in terms of metal based on the starting secondary alkyl-substituted naphthalenes. In contrast thereto, in the conventional method of using so-called non-homogeneous catalyst system, wherein palladium or gold as catalyst is dispersed either as metal itself or carried on solid carriers in the oxidation reaction system without dissolving it in the reaction mixture solution as in the present invention, the rate of oxidation of secondary alkyl-substituted naphthalenes is slow and in order to improve the oxidation rate according to this method, the amount of the non-homogeneous catalyst used must be markedly increased. On the contrary, the method of using the catalyst in the reaction mixture solution by dissolving said catalyst in the solvent to prepare a catalyst solution as in the case of the present invention, there is such an advantage that the catalyst used in very small amounts is sufficient to effect the oxidation reaction satisfactorily. When the amount of the metal compound dissolved in the reaction mixture solution is less than 0.5 ppm based on the starting secondary alkyl-substituted naphthalenes, the rate of oxidation of the naphthalenes is not improved so much. Therefore, the oxidation is carried out by using the metal compound in an amount of at least 0.5 ppm, preferably at least 2 ppm in the manner as mentioned above. In the present invention, no upper limit of the amount of the catalyst used is placed, but usually the catalyst is preferably used in an amount of less than 1000 ppm from the economical reason.

Usually, a pH of the reaction mixture solution is preferably at least 7, particularly at least 12. When the pH of the reaction mixture solution is 12 or higher, the oxidation rate can be markedly improved even when the amount of the metal compound as the catalyst, that is, the amount of the dissolved metal compound in the reaction mixture solution, is reduced.

The pH value of the reaction mixture solution may be determined by taking out a sample of 10–20 ml from the reaction mixture solution, followed by standing. Thereafter, an aqueous phase which separates therefrom is measured directly in pH. Where it is difficult to separate an aqueous phase from an oily phase, the pH measurement can be conducted by adding methyl isobutyl ketone saturated with water to the reaction mixture solution.

As mentioned above, the oxidation reaction rate can be improved when the pH of the reaction mixture solution is 12 or higher. In this sense, the use as the base in the oxidation reaction of such strong base as sodium hydroxide or the like is preferable since the pH of the reaction mixture solution can be made higher in comparison with the case of using such weak base as sodium hydrogen carbonate or the like.

Where the oxidation reaction is carried out after adjusting the pH of the reaction mixture solution to less than 12 by using as the base, for example, sodium carbonate or the like, the oxidation rate can be increased to practically the same level as attained by using the reaction mixture solution at a high pH value, when the oxidation reaction is effected by using the metal compound dissolved in the reaction mixture solution in an amount usually of at least 50 ppm in terms of metal based on the starting secondary alkyl-substituted naphthalenes.

In the present invention. molecular oxygen is used as an oxidizing agent, and usually air is used sufficiently as molecular oxygen. The amount of molecular oxygen used is not critical but usually 5–15 Nl/hr in terms of air. The oxidation reaction may be effected either batchwise or continuously.

In the present invention, the reaction temperature employed is usually 80°–150° C., preferably 90°–130° C., and the reaction time is usually 6–40 hours though it varies according to the conditions such as the reaction temperature and the like. The reaction is carried out usually under pressure, but, if necessary, can also be effected at ordinary pressure or under reduced pressure.

In the oxidation reaction of the secondary alkyl-substituted naphthalenes, a reaction initiator is preferably used. For instance, α,α-azobis(cyclohexane-1-carbonitrile) or hydroperoxides which are oxidation products of naphthalenes may be used as the reaction initiators, and the amount of such initiator used is usually 0.005–1 parts by weight based on 100 parts by weight of the reaction mixture.

In the present invention, the secondary alkyl-substituted naphthalenes are oxidized in the manner as mentioned previously to give hydroperoxides and/or carbinols. When 2,6-diisopropylnaphthalene is used, the resulting oxidation products include hydroperoxides such as 2,6-bis(2-hydroperoxy-2-propyl)naphthalene [another name of 2,6-diisopropylnaphthalene dihydroperoxide, hereinafter abbreviated to DHP], 2-(2-hydroxy-2-propyl)-6-(2-hydroperoxy-2-propyl)naphthalene [abbreviated to HHP], and 2-isopropyl-6-(2-hydroperoxy-2-propyl)naphthalene [abbreviated to MHP], and carbinols such as 2,6-bis(2-hydroxy-2-propyl)naphthalene [abbreviated to DCA], and 2-isopropyl-6-(2-hydroxy-2-propyl)naphthalene [abbreviated to MCA].

To obtain the composition of the reaction products resulting from the oxidation reaction, the mixture solution after the reaction is charged with alcohol or the like to prepare a homogeneous solution which is then assayed by liquid chromatography, whereby unreacted secondary alkyl-substituted naphthalenes and the oxidation reaction products such as DHP, HHP, DCA, MHP and MCA can be determined.

The total amount of hydroperoxides present in the oxidation reaction mixture (this means the sum total of amounts of DHP, HHP, MHP, etc., and hereinafter abbreviated to T-HPO) may be obtained by assaying the aforementioned organic phase by the known iodometry.

After the completion of the oxidation reaction, diisopropylnaphthalene dihydroperoxides contained in the oxidation reacton mixture as obtained is subjected to acid decomposition in the presence of acid catalysts to prepare the acid decomposition reaction product containing dihydroxynaphthalene. In that case, the starting material for the acid decomposition contains the aforesaid carbinols as the by-products of the oxidation reaction. Therefore, when a procedure is employed, if necessary, wherein hydrogen peroxide is made present simultaneously with the acid catalyst in practicing the acid decomposition reaction, HHP and DCA out of the by-product carbinols is oxidized to dihydroperoxides, and the dihydroperoxides is acid decomposed simultaneously with the acid catalyst, dihydroxynaphthalene can be obtained in high yields.

Where the rate of reaction of diisopropylnaphthalene is raised to 80% or higher, besides DHP, the yields of HHP and DCA also increase, but said HHP DCA can be converted to DHP when the above-mentioned procedure wherein hydrogen peroxide is made present simultaneously with the acid catalyst at the time of effection the acid decomposition reaction, and hence dihydroxynaphthalene can be contained in high yields. In this case, moreover, the yield of MHP which does not contribute to the formation of dihydroxynaphthalene can be desirably decreased. By raising the rate of reaction of diisopropylnaphthalene to more than 90%, more preferably more than 95%, the yields of dihydroxynaphthalene can be further increased.

The acid decomposition reaction as mentioned above is preferably carried out in the presence of at least one solvent selected from (a) nitriles, nitro compounds, phenols and halogenated hydrocarbons.

Useful nitriles concretely include aliphatic nitriles such as acetonitrile, propionitrile, butyronitrile, hexanenitrile, etc., aliphatic dinitriles such as malonitrile, succinonitrile, adiponitrile, etc., and aromatic nitriles such as benzonitrile, tolunitrile, etc.

Useful nitro compound concretely include aliphatic and alicyclic nitro compounds such as nitromethane, nitroethane, nitrocyclohexane, etc., and aromatic nitro compounds such as nitrobenzene, nitrotoluene, dinitrotoluene, nitrophenol, etc.

Useful phenols concretely include monovalent phenols such as phenol, m- or p-cresol, mixed cresol, ethyl phenol, m- or p-isopropylphenol, etc. and polyvalent phenols such as resorcin, chloroglucin, 2,6-dihydroxynaphthalene, etc.

Concretely exemplified as halogenated hydrocarbons are dichloromethane, dibromomethane, chloroform, dichloroethane, etc.

Such solvents as exemplified above may be used in an amount of 0.5-100 parts by weight, preferably 1-50 parts by weight based on 1 part by weight of the total sum of amounts of hydroperoxides and carbinols. The use of these solvent in an amount of less than 0.5 part by weight is not preferable because the selectivity and yield of hydroxynaphthalene decrease. On the one hand, the upper limit of the amount of the solvent used is not critical, but the amount of the solvent is desirably in the above-mentioned range from the economical reason.

As mentioned previously, the acid decomposition reaction referred to above is preferably carried out in the presence of (b) hydrogen peroxide.

As hydrogen peroxide mentioned above, there may be used, in addition to hydrogen peroxide or aqueous hydrogen peroxide solutions, such substances which generate hydrogen peroxide under the reaction conditions, for example, as sodium peroxide, calcium peroxide, etc., but the aqueous hydrogen peroxide solutions are preferably used. Particularly, by using hydrogen peroxide at the time of the acid decomposition reaction in an amount of 0.9-2 moles, preferably 1.0-1.5 moles per 1 mole of the alcoholic hydroxyl group of the above-mentioned carbinols, the desired dihydroxynaphthalene can be obtained in high yields. Furthermore, the use of hydrogen peroxide under such conditions is preferable since the formation of byproducts resulting from the condensation of carbinols can be markedly suppressed at the same time.

Preferably usable as (c) acid used in the acid decomposition reaction are inorganic acids such as sulfuric acid, hydrochloric acid, hydrogen fluoride, phosphoric acid, etc., solid acids such as strong acidic ion exchange resins, silica gel, silica alumina, etc., organic acids such as chloroacetic acid, methanesulfonic acid, benzenesulfonic acid, toluenesulfonic acid, etc., and heteropolyacids such as phosphotungstic acid, phosphomolybdic acid, etc. These (c) acids may be added as they are to the reaction system, or may be added after dissolving them in suitable inert solvents when the acids have solubility. The amount of (c) acid is usually in the range of 0.01-10% by weight based on the whole reaction mixture, though it may depend on the kind of acid used and the reaction conditions used in the acid decomposition reaction.

This acid decomposition reaction is carried out at a temperature ranging from 0° to 100° C., preferably from 20° to 80° C.

To the acid decomposition reaction mixture containing hydroxynaphthalene, particularly dihydroxynaphthalene, is added an acyloxylating agent, and the hydroxynaphthalene is reacted with the acyloxylating agent in the presence of the catalyst to prepare acyloxynaphthalene. In that case, when the acyloxylation reaction is effected, such low boiling substance as the byproduct acetone and the reaction solvent may suitably be removed by distillation from the acid decomposition reaction mixture, if necessary.

The acyloxylating agent is preferably added to the acid decomposition reaction mixture in an amount of 1-20 moles, preferably 2-5 moles per 1 mole of the hydroxynaphthalene contained in the acid decomposition reaction product.

The acyloxylating agent used in the present invention include anhydrous lower aliphatic carboxylic acids such as anhydrous formic acid, anhydrous acetic acid, anhydrous propionic acid, anhydrous butyric acid, anhydrous valeric acid, etc., anhydrous aromatic carboxylic acids such as anhydrous benzoic acid, anhydrous toluic acid, etc., and acid chlorides such as acetyl chloride, etc.

The catalysts used in effecting the reaction of the hydroxynaphthalene with the acyloxylating agent include such acid catalysts as used in the decomposition of diisopropylnaphthalene dihydroperoxide, and particularly preferred are inorganic acids such as sulfuric acid, hydrochloric acid, phosphoric acid, bron fluoride, etc. Ion exchange resins as solid acids may also be used. In addition to the acids, preferably usable as the catalysts are such organic bases as pyridine, quinolin, etc., and such salts as sodium acetate, etc. Usually, the amount of the catalyst used is preferably in the range of 0.01-10% by weight based on the whole reaction mixture, though it may vary depending on the kind of the catalyst used and the conditions employed.

The reaction between the hydroxynaphthalene and the acyloxylating agent such as anhydrous carboxylic acid is carried out at the reaction temperature ranging from 0° to 200° C., preferably from 80° to 140° C., and the reaction time is from 30 minutes to 5 hours, preferably from 1 to 2 hours.

After addition to the acid decomposition reaction product containing the hydroxynaphthalene of the acyloxylating agent such as anhydrous carboxylic acid, the hydroxynaphthalene is reacted with the acyloxylating agent such as anhydrous carboxylic acid, and the resulting reaction mixture is cooled by spontaneous cooling or the like, whereby acyloxynaphthalene is obtained as a precipitate from the reaction mixture.

Acyloxylation of the acid decomposition product may be carried out in the presence of aromatic hydrocarbons such as cumene, dialkyl ketones such as methyl isobutyl ketone. Particularly, the acyloxylation carried out by using methyl isobutyl ketone as the solvent is preferable, because impurities are extracted with the solvent and remain in the reaction system when the desired acyloxynaphthalene is separated from the reaction mixture, the purity of the resulting acyloxynaphthalene become higher.

The acyloxy group of the acyloxynaphthalene is represented by the general formula

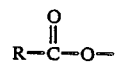

wherein R represents lower alkyl or aryl, and said acyloxy group concretely includes formyloxy, acetoxy, propionyloxy, butyryloxy, valeryloxy, benzoyloxy, toluyloxy, etc.

The acyloxynaphthalene, particularly diacyloxynaphthalene, is found to be a very excellent product having the purity of higher than 99%, and the rate of reaction of diacyloxynaphthalene based on dihydroxynaphthalene is very favorable as evidence by the reaction rate of 99 mol % and, moreover, the yield of crystalline diacyloxynaphthalene is excellent as evidence by the yield of 95 mol %.

EFFECT OF THE INVENTION

According to the process for preparing hydroxynaphthalene of the present invention, not only the amount of catalyst used can be reduced but also the oxidation rate can be marked improved, and hence the oxidation products hydroperoxides and carbinols can be obtained in high yields.

According to the process for preparing hydroxynaphthalene of the present invention, from the oxidation reaction mixture obtained in the manner mentioned above which contains hydroperoxides and/or carbinols, the hydroperoxides can be obtained in high yields as well as in high purity.

The process of the present invention is illustrated below with reference to examples, but it should be construed that the invention is in no way limited to those examples.

EXAMPLE 1

Into a 5000 ml autoclave equipped with a rotary agitator (turbine blade type stirring blades), a gas blowing pipe, a thermometer sheath and reflux condenser were charged 1100 g of 2,6-diisopropylnaphthalene, 300 g of an aqueous solution of 4.6% by weight of sodium hydroxide, 850 g of water, 11 g of a reaction initiator (hydroperoxide of 2,6-diisopropylnaphthalene), and 50 g of a catalyst solution of a concentration of 23 ppm in terms of Pd metal obtained by dissolving palladium chloride in an aqueous solution of 4.5% by weight of sodium hydroxide. The mixture was allowed to undergo reaction by stirring the autoclave at 1000 rpm for 8 hours while blowing air thereinto at a rate of 195 Nl/hr. At that time, a pH of the reaction mixture at the outset of the reaction was about 14, and that measured at the completion of the reaction was 13.3. The palladium chloride charged as the catalyst was found to be totally dissolved in the reaction mixture, and the amount of said compound in terms of Pd was 1.1 ppm based on the weight of the starting 2,6-diisopropylnaphthalene.

The results obtained are shown in Table 1.

COMPARATIVE EXAMPLE 1

The oxidation of Example was repeated except that charged into the autoclave was a mixture of 1800 g of 2,6-diisopropylnaphthalene, 350 g of the aqueous solution of 4.5% by weight of sodium hydroxide, 150 g of water and 18 g of the reaction initiator but excluding the metal compound as the catalyst, and the reaction was carried out at 100° C.

The results obtained are shown in Table 1.

EXAMPLE 2

Following the same procedure as described in Comparative Example 1, the reaction was carried out except that into the autoclave were charged 1150 g of 2,6-diisopropylnaphthalene, 7.0 g of granular sodium hydroxide, 1150 g of water, 46 g of the reaction initiator and the catalyst solution having the Pd concentration of 1000 ppm obtained by dissolving palladium chloride in a 1% aqueous sulfuric acid solution.

The results obtained are shown in Table 1.

EXAMPLE 3

Following the same procedure as described in Comparative Example 1, the reaction was carried out except that into the autoclave were charged, in addition to 1800 g of 2,6-diisopropylnaphthalene, 248 g of the aqueous solution of 4.5% by weight of sodium hydroxide, 206 g of water and 46 g of the catalyst solution having the Pd concentration of 100 ppm obtained by dissolving palladium sulfate as the catalyst in a 10% aqueous sodium hydroxide solution.

The results obtained are shown in Table 1.

EXAMPLE 4

Following the same procedure as described in Comparative Example 1, the oxidation was carried out except that into the autoclave were charged 1100 g of 2,6-diisopropylnaphthalene, 350 g of the aqueous solution of 4.5% by weight of sodium hydroxide and 850 g of water at 90° C. while feeding the catalyst solution having the Pd concentration of 100 ppm obtained by dissolving palladium chloride in an aqueous solution of 10% by weight of sodium hydroxide at a rate of 10 ml per hour.

The results obtained are shown in Table 1.

COMPARATIVE EXAMPLE 2

Following the same procedure as described in Comparative Example 1, the reaction was carried out except that into the autoclave were charged 330 g of the aqueous solution of 4.5% by weight of sodium hydroxide and 20 g of the catalyst solution having the Pd concentration of 23 ppm obtained by dissolving palladium chloride in an aqueous solution of 4.5% by weight of sodium hydroxide in addition to 1800 g of 2,6-diisopropylnaphthalene, 150 g of water and 18 g of the reaction initiator.

The results obtained are shown in Table 1.

COMPARATIVE EXAMPLE 3

Following the same procedure as described in Example 3, the reaction was carried out except that in place of the catalyst solution having dissolved therein palladium chloride in the aqueous sodium hydroxide solution, used was 0.186 g of Pd black fine powder as the catalyst, the solid contents Pd in 2,6-diisopropylnaphthalene having been adjusted to become 100 ppm. After the completion of the reaction, an oily phase and aqueous phase of the reaction mixture were filtered to assay the amount of said Pd compound by the atomic-absorption spectroscopy, whereby lrace amounts of Pd were determined.

The results obtained are shown in Table 1.

COMPARATIVE EXAMPLE 4

Following the same procedure as described in Comparative Example 1, the reaction was carried out except that into the autoclave were charged 1800 g of 2,6-diisopropylnaphthalene, 248 g of the aqueous solution of 4.5% by weight of sodium hydroxide, 206 g of water and 4.6 g of a catalyst solution obtained by dissolving NaAuCl$_4$ in an aqueous solution of 10% by weight of sodium hydroxide so that the amount of Au became 0.25 ppm based on the weight of said naphthalene present in the reaction mixture.

The results obtained are shown in Table 1.

EXAMPLE 5

The same procedure as described in Comparative Example 4 was repeated except that the amount of Au in the reaction mixture was adjusted to 2.6 ppm.

The results obtained are shown in Table 1.

COMPARATIVE EXAMPLES 5–8

Following the same procedure as described in Comparative Example 4, the reaction was carried out except that various metal compounds as shown in Table 1 were respectively dissolved in the aqueous solution of 4.5% by weight of sodium hydroxide to prepare catalyst solutions each containing 100 ppm, calculated as metal, of the metal compounds, and the catalyst solution were individually charged into the reaction system so that the amount of said metal in the reaction mixture was adjusted to 2.6 ppm based on the charged weight of 2,6-diisopropylnaphthalene.

The results obtained are shown in Table 1.

COMPARATIVE EXAMPLE 9

Following the same procedure as described in Comparative Example 1, the reaction was carried out for 8 hours at 100° C., except that into the autoclave were charged 1150 g of 2,6-diisopropylnaphthalene, 9.2 g of sodium carbonate as a base in place of the aqueous sodium hydroxide solution, 1150 g of water and 46 g of the reaction initiator.

The results obtained are shown in Table 2.

palladium chloride as the catalyst in a 1% aqueous sulfuric acid solution so as to have the palladium chloride concentration of 1000 ppm was charged into the autoclave so that the amount of Pd in the reaction mixture became 100 ppm based on the charged 2,6-diisopropylnaphthalene.

The results obtained are shown in Table 2.

COMPARATIVE EXAMPLE 11

Following the same proceduce as described in Comparative Example 9, the reaction was carried out except that 115 g of a catalyst solution obtained by dissolving $PtCl_4.5H_2O$ as the catalyst in a 1% aqueous sulfuric acid solution so as to have a concentration as Pt of 900 ppm was charged into the autoclave so that the amount of Pt in the reaction mixture became 100 ppm based on the charged amount of 2,6-diisopropylnaphthalene.

The results obtained are shown in Table 2.

TABLE 1

| Experiment | Temperature (°C.) | pH | Catalyst (ppm based on DIPN) | | | Reaction result yield (mol %) | | | | |
| | | | Metal compound | Amount charged | Dissolved amount | T-HPO (wt %) | DHP | HHP | MHP | DIPN |
| --- | --- | --- | --- | --- | --- | --- | --- | --- | --- | --- |
| Compar. Example 1 | 100 | 14 13.5 | no catalyst | 0 | 0 | 55.7 | 6.2 | 2.5 | 39.9 | 45.7 |
| Compar. Example 2 | 100 | 14 13.3 | $PdCl_2$ | Liquid 0.26 | 0.26 | 56.7 | — | — | — | — |
| Example 1 | 95 | 14 13.3 | $PdCl_2$ | Liquid 1.1 | 1.1 | 65 | — | — | — | — |
| Compar. Example 3 | 100 | 14 13.3 | Pd black | Solid 100 | trace | 71.1 | 11.8 | 3.5 | 40.9 | 33.8 |
| Example 2 | 100 | 14 11.8 | $PdCl_2$ | Liquid 2.0 | 2.0 | 76.7 | 12.5 | 4.5 | 41.7 | 29.7 |
| Example 3 | 100 | 14 13.6 | $PdSO_4$ | Liquid 2.6 | 2.6 | 82.0 | 15.3 | 6.3 | 40.1 | 24.6 |
| Example 4 | 90 | 14 13.2 | $PdCl_2$ | Liquid 6.9 | 6.9 | 60.4 | 6.4 | 1.3 | 39.8 | 48.8 |
| Compar. Example 4 | 100 | 14 | $NaAuCl_4$ | Liquid 0.25 | 0.25 | 40.8 | — | — | — | — |
| Example 5 | 100 | 14 13.4 | $NaAuCl_4$ | Liquid 2.6 | 2.6 | 66.0 | 9.4 | 4.4 | 40.9 | 36.0 |
| Compar. Example 5 | 100 | 14 13.8 | $RhCl_3\ 3H_2O$ | Liquid 2.6 | 2.6 | 47.1 | 3.4 | 1.2 | 34.6 | 57.1 |
| Compar. Example 6 | 100 | 14 13.8 | $PtCl_4\ 5H_2O$ | Liquid 2.6 | 2.6 | 49.5 | 4.7 | 1.8 | 37.6 | 51.6 |
| Compar. Example 7 | 100 | 14 13.6 | $NaIrCl_6$ | Liquid 2.6 | 2.6 | 42.0 | 3.8 | 1.4 | 34.9 | 56.5 |
| Compar. Example 8 | 100 | 14 13.7 | $KReO_4$ | Liquid 2.6 | 2.6 | 43.8 | 3.4 | 1.3 | 33.8 | 58.3 |

Base Aq.: NaOH solution used.
Reaction time 8 hr.

TABLE 2

| Experiment | Temperature (°C.) | pH | Catalyst (ppm based on DIPN) | | | Reaction result yield (mol %) | | | | |
| | | | Metal compound | Amount charged | Dissolved amount | T-HPO (wt %) | DHP | HHP | MHP | DIPN |
| --- | --- | --- | --- | --- | --- | --- | --- | --- | --- | --- |
| Compar. Example 9 | 100 | 11.2 10.2 | no catalyst | 0 | 0 | 50.5 | 4.1 | 1.6 | 34.4 | 52.7 |
| Compar. Example 10 | 100 | 11.2 10.2 | Rh black | Solid 100 | tr | 51.1 | 4.6 | 1.5 | 35.7 | 52.6 |
| Example 6 | 100 | 11.2 8.5 | $PdCl_2$ | Liquid 100 | 100 | 106.3 | 26.0 | 11.1 | 34.4 | 10.0 |
| Compar. Example 11 | 100 | 11.2 10.4 | $PtCl_4\ 5H_2O$ | Liquid 90 | 90 | 25.8 | 1.7 | 1.2 | 23.7 | 70.0 |

Base Aq.: NaOH solution used.

COMPARATIVE EXAMPLE 10

Following the same procedure as described in Comparative Example 10, the reaction was carried out except that the palladium black as the catalyst was dispersed in an amount that it became 100 ppm based on the 2,6-diisopropylnaphthalene.

The results obtained are shown in Table 2.

EXAMPLE 6

Following the same procedere as described in Comparative Example 9, the reaction was carried out except that 115 g of a catalyst solution obtained by dissolving

EXAMPLE 7

Into a reactor were charged 3000 parts by weight of 2,6-diisopropylnaphthalene (2,6-DIPN)(purity: 2,6-DIPN 99.0%, 2,7-DIPN 0.8%), 6000 parts by weight of an aqueous solution of 4.5% by weight of sodium hydroxide, 10 mg of palladium chloride and 10 g of an oxidation product of 2,6-DIPN. The reaction was carried out for 23 hours at 100° C. and a pressure of 5 kg/cm² G by stirring the contents of the reactor while blowing thereinto air at a rate of 1 N m³/hr. After the completion of the reaction, 6000 parts by weight of methyl isobutyl ketone (MIBK) was added to the reaction mixture, an alkali aqueous layer separated was removed therefrom, an oily layer obtained was washed with water and then subjected to azeotropic dehydration to obtain a composition as shown in Table 3.

TABLE 3

| Component | Composition (Wt %) |
|---|---|
| DHP | 13.1 |
| HHP | 14.6 |
| DC | 4.0 |
| MIBK | 58.2 |
| MC | 1.7 |
| Others | 8.4 |

Into a flask equipped with an agitator, a reflux condenser and a thermometer were charged 0.05 g of sulfuric acid and 19.0 g of acetonitrile, and the contents of the flask was heated on a hot water bath kept at 50° C. Into the flask were respectively fed for 1 hour 25.6 g of an acetonitrile solution containing 6.6 g of hydrogen peroxide, and a mixture of 100 g of MIBK solution of 2,6-DIPN oxide having the composition shown in Table 3 obtained in the manner mentioned above and 47.3 g of acetonitrile through separate feed pipes by constant delivery pumps ($H_2O_2$/carbinol molar ratio is 1.2, ratio of sulfuric acid to DHP+HHP+DC is 0.16 wt %). Thereafter, the reaction was continued for 1 hour. The reaction product was assayed for 2,6-DHN by liquid chromatography to find that the yield of 2,6-DHN was 97%.

Yield of 2,6-DHN =

$$\frac{DHN \text{ (mole number)}}{\text{Mole number of (DHP + HHP + DC)}} \times 100$$

EXAMPLE 8

The MIBK solution of 2,6-DIPN oxide obtained in Example 7 was distilled under reduced pressure, and toluene was added to the residue. The operation was repeated twice, and MIBK was substituted with toluene. The solution obtained was found to contain 34.9% of oxide and 65.1% of solvent.

Subsequently, into the same flask as in Example 7 were charged 0.05 g of sulfuric acid and 9.5 g of acetonitrile, and the contents of the flask was heated on a hot water bath kept bath 50° C. Into the flask were respectively fed for 1 hour 35.8 g of an acetonitrile solution containing 5.8 g of 60% hydrogen peroxide ($H_2O_2$/carbinol molar ratio was 1.2, proportion of sulfuric acid to oxide was 0.13 wt %), and a mixture of 110 g of a toluene solution of 2,6-DIPN oxide obtained in the manner mentioned above and 22.9 g of acetonitrile through separate feed pipes by constant delivery pumps. Thereafter, the reaction was continued for 1 hour. The yield of 2,6-DHN was quantitatively 99% or higher.

EXAMPLE 9

Example 8 was repeated except that the 60% hydrogen peroxide was used in an amount of 5.0 g ($H_2O_2$/carbinol molar ratio was 1.0). The yield of 2,6-DHN was 95%.

EXAMPLE 10

Example 8 was repeated except that the 60% hydrogen peroxide was used in an amount of 4.5 g ($H_2O_2$/carbinol molar ratio was 0.0). The yield of 2,6-DHN was 82%.

COMPARATIVE EXAMPLE 12

The same procedure as in Example 8 was carried out but using dioxane in place of the acetonitrile, to obtain a solution containing 34.2% of oxide and 65.8% of solvent. Thereafter, the same procedure as in Example 8 was repeated by using the solution obtained above. The yield of 2,6-DHN was 65%.

EXAMPLE 11

Into a 100 ml round flask were charged 2.0 g of 2,6-diacetoxynaphthalene, 20 g of methanol as a solvent, 1.5 g of water and 0.12 g of concentrated sulfuric acid as an acid catalyst. The reaction was carried out for 5 hours at 65° C. in nitrogen atmosphere while stirring the mixture with a magnetic stirrer. The reaction liquid was assayed by gas chromatography, whereby 2,6-dihydroxynaphthalene formed was 5.5% by weight (reaction yield 99%) and 2,6-dihydroxynaphthalene dimer 0.01% by weight.

EXAMPLES 12-15

Example 11 was repeated except that the solvents and reaction temperatures employed were changed from those employed Example 11. The results obtained are shown in Table 4.

COMPARATIVE EXAMPLES 13-14

Example 11 was repeated except that the solvents and reaction temperatures employed were changed from those employed in Example 11. The results obtained are shown in Table 4.

TABLE 4

| Example (Compar. Example) | Solvent | Reaction temperature (°C.) | Reaction yield of 2,6-dihydroxy-naphthalene (wt %) |
|---|---|---|---|
| Ex. 12 | Acetic acid | 80 | 98 |
| Ex. 13 | Methyl acetate | 60 | 97 |
| Ex. 14 | Dioxane | 80 | 97 |
| Ex. 15 | Acetonitrile | 78 | 95 |
| Compar. Ex. 13 | Toluene | 80 | 2 |
| Compar. Ex. 14 | Methyl isobutyl ketone | 76 | 87 |

EXAMPLE 16

Into the same flask as in Example 11 were charged 2.0 g of 2,6-diacetoxynaphthalene, 20 g of methanol, 0.3 g of water and 0.12 g of concentrated sulfuric acid. The reaction was carried out for 5 hours in nitrogen atmosphere at 65° C., while stirring the contents of the flask. The reaction yield of 2,6-dihydroxynaphthalene was 97%.

EXAMPLE 17-18

Example 16 was repeated except that the catalysts shown in Table 5 were used in place of the concentrated sulfuric acid. The results obtained are shown in Table 5.

TABLE 5

| Example | Catalyst | Reaction yield of 2,6-dihydroxynaphthalene (wt %) |
| --- | --- | --- |
| 16 | Sulfuric acid | 97 |
| 17 | Hydrochloric acid | 95 |
| 18 | Zinc chloride | 94 |

COMPARATIVE EXAMPLE 15

Example 16 was repeated except that sodium hydroxide was used in place of the concentrated sulfuric acid. According to assay of the reaction liquid by gas chromatography, 2,6-dihydroxynaphthalene was 4.9% by weight (reaction yield 84%), and 2,6-dihydroxynaphthalene dimer was 0.9% by weight.

COMPARATIVE EXAMPLE 16

Example 16 was repeated except that phosphoric acid was used in place of the concentrated sulfuric acid. 2,6-Dihydroxynaphthalene formed was 0.28% by weight (reaction yield 5%), and 2,6-diacetoxynaphthalene remained in large amounts as unreacted product.

What is claimed is:

1. A process for preparing hydroxynaphthalene which comprises subjecting secondary alkyl-substituted naphthalenes to liquid phase oxidation with molecular oxygen to form hydroperoxides and/or carbinols at a temperature ranging from 80°–150° C. and then obtaining the hydroxynaphthalene from the hydroxyperoxides and/or carbinols by an acid decomposition reaction at a temperature ranging from 0° to 100° C., wherein the oxidation reaction is carried out by dissolving in the reaction mixture of the secondary alkyl-substituted naphthalenes, at least 0.5 ppm in terms of metal, based on the starting secondary alkyl-substituted naphthalenes, of at least one compound of metal selected from the group consisting of palladium and gold, said metal compound being soluble in the reaction mixture of the secondary alkyl-substituted naphthalenes and alkaline water.

2. The process as claimed in claim 1 wherein the secondary alkyl-substituted naphthalene is 2,6-diisopropylnaphthalene.

3. The process as claimed in claim 1 wherein the palladium compound is palladium chloride, palladium sulfate, palladium nitrate, palladium acetylacetonate or palladium oxalate, and the gold compound is sodium aurichloride, gold cyanide, gold chloride, potassium tetrachloroaurate, sodium tetrachloroaurate or potassium tetrahydroxyaurate.

4. The process as claimed in claim 1 wherein the oxidation reaction mixture obtained is decomposed with (c) an acid in the presence of at least one solvent selected from (a) nitriles, nitro compounds, phenols and halogenated hydrocarbons, and of (b) hydrogen peroxide.

5. The process as claimed in claim 4 wherein an acyloxylating agent is added to the acid decomposition reaction mixture, the hydroxynaphthalene present in said reaction mixture is reacted with the acyloxylating agent in the presence of a catalyst to form acyloxynaphthalene, and then the acyloxynaphthalene is hydrolyzed in a solvent containing water in the presence of an acid catalyst to form the hydroxynaphthalene.

* * * * *